(12) United States Patent
Hendriksen et al.

(10) Patent No.: US 6,559,248 B2
(45) Date of Patent: May 6, 2003

(54) PROCESS OF REMOVING CONTAMINANTS FROM AN OLEFIN STREAM USING EXTRACTIVE DISTILLATION

(75) Inventors: Dan E. Hendriksen, Phillipsburg, NJ (US); Minquan Cheng, Evansville, IN (US); Keith H. Kuechler, Friendswood, TX (US); David R. Lumgair, Craddockville, VA (US); Michael P. Nicoletti, Houston, TX (US); Richard Shutt, Tervuren (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 09/943,695

(22) Filed: Aug. 31, 2001

(65) Prior Publication Data

US 2003/0045655 A1 Mar. 6, 2003

(51) Int. Cl.⁷ ............................ C08F 10/06; C07C 7/08
(52) U.S. Cl. ................ 526/77; 585/639; 585/836; 585/864; 585/868; 203/63; 203/66; 203/95
(58) Field of Search ................. 585/639, 864, 585/868, 836; 203/63, 66, 95; 526/77

(56) References Cited

U.S. PATENT DOCUMENTS

| | | | | |
|---|---|---|---|---|
| 3,847,793 | A | | 11/1974 | Schwartz et al. .............. 208/70 |
| 3,969,426 | A | | 7/1976 | Owen et al. ............. 260/668 R |
| 4,035,430 | A | | 7/1977 | Dwyer et al. ........... 260/668 R |
| 4,053,534 | A | | 10/1977 | Mitchell et al. .... 260/683.15 R |
| 4,058,576 | A | | 11/1977 | Chang et al. ................ 260/673 |
| 4,542,252 | A | | 9/1985 | Graziani et al. ............. 585/640 |
| 4,814,517 | A | | 3/1989 | Trubac ...................... 568/697 |
| 4,849,575 | A | | 7/1989 | Lewis ......................... 585/640 |
| 5,000,825 | A | * | 3/1991 | Shih et al. ...................... 203/3 |
| 5,569,788 | A | * | 10/1996 | Forte et al. ............. 585/809 X |
| 5,573,990 | A | | 11/1996 | Wang et al. .................. 502/77 |
| 6,049,017 | A | | 4/2000 | Vora et al. ................... 585/324 |
| 6,121,504 | A | | 9/2000 | Kuechler et al. ............ 585/640 |
| 6,143,936 | A | * | 11/2000 | Marion et al. .......... 585/640 X |

* cited by examiner

*Primary Examiner*—Fred Teskin
(74) *Attorney, Agent, or Firm*—Paul T. Lavoie

(57) ABSTRACT

Disclosed is a method of purifying olefin containing oxygenate contaminants. The method incorporates the use of extractive distillation. Under the appropriate conditions, olefins containing very low levels of oxygenate contaminants can be recovered.

26 Claims, 1 Drawing Sheet

PROCESS OF REMOVING CONTAMINANTS FROM AN OLEFIN STREAM USING EXTRACTIVE DISTILLATION

FIELD OF THE INVENTION

This invention relates to removing oxygenates from an olefin stream. In particular, this invention relates to removing oxygenates using extractive distillation.

BACKGROUND OF THE INVENTION

Olefins, particularly light olefins such as ethylene and propylene, have been traditionally produced from petroleum feedstocks by either catalytic or steam cracking. Oxygenates, however, are becoming an alternative feedstock for making light olefins.

The process of producing olefins from an oxygenate source instead of a higher hydrocarbon source, as in catalytic or steam cracking, can create a variety of problems concerning certain oxygenated contaminates in the olefin product stream. The task of removing these oxygenated contaminates from an olefin containing product stream is a unique and difficult task.

U.S. Pat. No. 6,121,504 discloses a process for directly quenching a gas phase product stream from an oxygenate to olefin process. The direct quenching process causes higher boiling components, such as water and unreacted oxygenate feedstock, to condense and form a heavy product fraction. The heavy product fraction is separated from the lighter olefin product fraction, and the olefin product fraction can be further processed.

Although processes such as direct quenching processes can remove a large percentage of oxygenated components from the light olefin product of an oxygenate to olefin process, a certain amount of oxygenate can nevertheless remain with recovered olefin product. If it is desired to further react the recovered olefins to produce derivative products, the oxygenate contaminants can be problematic in such reaction processes. For example, if it is desired to produce a polyolefin from the olefin product, certain oxygenates may poison the polyolefin catalysts used to make the polyolefin at levels as low as low as 1 ppm. Therefore, it is desirable to remove oxygenate contaminants from olefin containing streams to levels lower than conventional quenching processes can provide.

SUMMARY OF THE INVENTION

This invention provides the ability to remove substantially all oxygenate contaminants from an olefin containing stream using extractive distillation. The resulting purified olefin is particularly suitable for use as feed in the manufacture of polyolefins.

Specifically, the invention provides a method of extracting an oxygenate from an olefin containing stream. The method comprises contacting the olefin containing stream with an extractant; and separating the contacted olefin containing stream and extractant using extractive distillation. The olefin containing stream most suitable for the process comprises at least 50 wt. % olefins and not greater than 20 wt. % oxygenates prior to contact with the extractant. Preferably, the extractant is a polar liquid composition at 1 atm., having an average boiling point of at least 100° F. (38° C.) at 1 atm. More preferably, the polar liquid composition comprises at least 75 wt. % water, alcohol, or a mixture thereof.

The extractive distillation process is particularly effective when operating at pressures higher than conventional quench type processes. Desirably the extractive distillation is carried out at a pressure of from about 100 psia to about 5000 psia.

The invention further provides a method of purifying an olefin containing stream. The method comprises contacting the olefin containing stream with a water containing stream in a first vessel; recovering olefin product from the first vessel; and contacting the olefin product from the first vessel with an extractant in a second vessel at a temperature and pressure higher than that of the first vessel. This embodiment is particularly effective when the olefin containing stream, prior to contact with the extractant, comprises at least 50 wt. % ethylene and propylene, and the extractant is a polar liquid composition at 1 atm., having an average boiling point of at least 100° F. (38° C.) at 1 atm.

The invention is also directed to a method of purifying and polymerizing an olefin containing stream. This embodiment comprises contacting the olefin containing stream with a water containing stream in a first vessel; recovering olefin product from the first vessel; contacting the olefin product from the first vessel with an extractant in a second vessel at a temperature and pressure higher than that of the first vessel; recovering olefin product from the second vessel; and polymerizing at least one olefin recovered from the second vessel. It is desirable that the olefin containing stream, prior to contact with the extractant, comprises at least 50 wt. % ethylene and propylene, and the extractant is a polar liquid composition at 1 atm., having an average boiling point of at least 100° F. (38° C.) at 1 atm.

BRIEF DESCRIPTION OF THE DRAWING

One embodiment of the overall invention is shown in the attached FIGURE, which depicts a flow diagram of an integrated water quench and extractive distillation process.

DETAILED DESCRIPTION OF THE INVENTION

Figure 1:
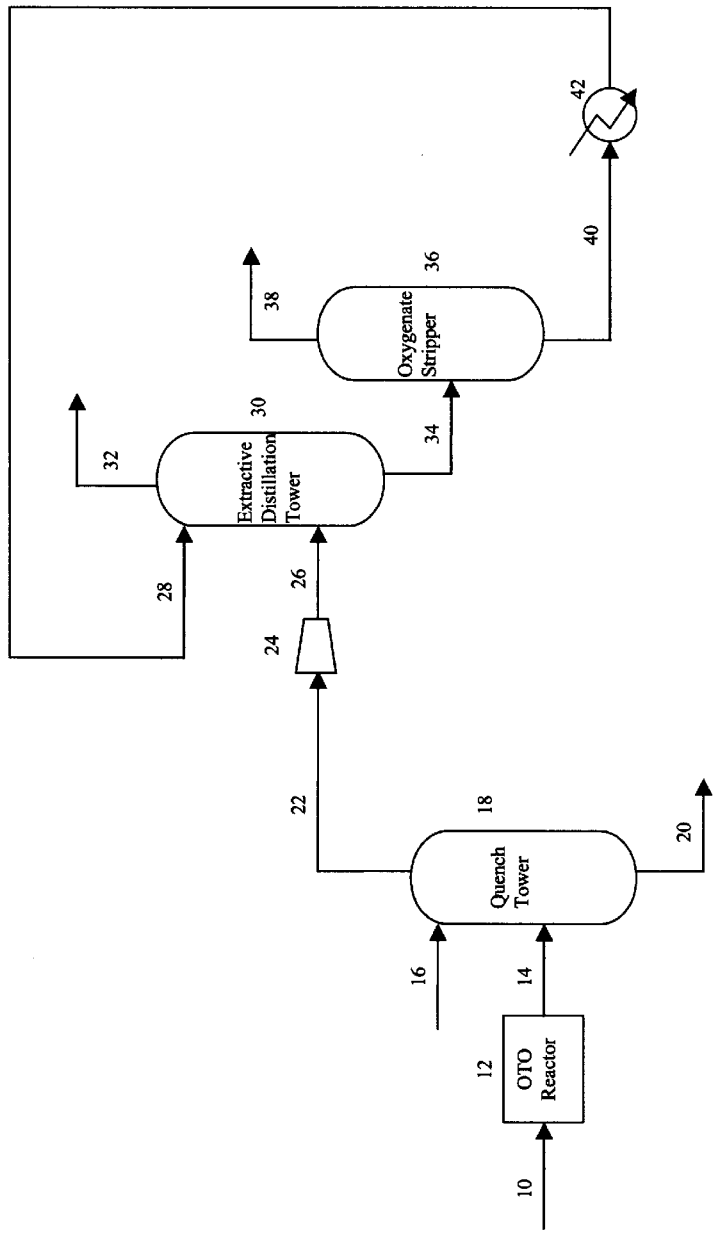

This invention is to a process for purifying olefin streams. In particular, the invention is to a process for extracting oxygenate contaminants from olefin containing streams. The invention is particularly effective in removing oxygenates which can accompany light olefin product, particularly ethylene and propylene, recovered from an oxygenate to olefins process. However, the invention is effective for removing oxygenate contaminants from olefin streams, regardless of how the olefin stream was obtained.

The invention is particularly effective for removing oxygenate contaminants from olefin streams which contain at least about 50 wt. % olefin, more particularly at least about 60 wt. % olefin, and more particularly at least about 70 wt. % olefin. It is particularly advantageous when the total olefin content of the olefin stream comprises at least about 60 wt. % ethylene and propylene, more particularly at least about 70 wt. % ethylene and propylene, and most particularly at least about 80 wt. % ethylene and propylene.

In order to remove certain desired oxygenate contaminants from an olefin containing stream down to the ppm level, the invention incorporates the use of extractive distillation. In cases where contaminants are at a relatively high level, it is desirable to first use a quench process to remove a substantial quantity of the contaminants, then to follow the quench process using extractive distillation.

A quench process involves contacting the olefin containing stream with a quench liquid. The quench liquid is directly contacted with the olefin stream so as to cool the stream to a temperature below the condensation temperature of the quench liquid, preferably below the condensation temperature of oxygenate contaminant in the olefin containing stream.

The quench liquid can be any fluid that is a liquid at 1 atm. and is capable of removing oxygenate contaminants. Water is a preferred quench medium in this invention.

In one embodiment of the invention, a sufficient quantity of water is added to the top of a quench vessel or column. An olefin containing stream containing oxygenate contaminant is added to the bottom of the quench column. As the olefin rises up the quench column, it comes in direct contact with quench water moving down the quench column. The olefin passes from the quench column in the gaseous state as an overhead product, and with a substantial quantity of oxygenate contaminant being removed. The oxygen contaminant is removed with the quench fluid as a bottoms stream from the quench tower.

The function of the quench process is to cool the olefin steam which contains the oxygenate contaminants so that the contaminants condense. Once the contaminants condense, they can be relatively easily separated from the olefin stream.

It is desirable that the operating temperature of the quench process be from about 80° F. (27° C.) to about 500° F. (260° C.); preferably from about 85° F. (29° C.) to about 300° F. (149° C.); more preferably from about 90° F. (32° C.) to about 200° F. (93° C.). It is also desirable that the operating pressure of the quench process be from about 15 psia (103 kPa) to less than about 100 psia (689 kPa); preferably from about 15 psia (103 kPa) to about 75 psia (517 kPa); and more preferably from about 15 psia to about 50 psia (345 kPa).

Many oxygenate contaminants are water soluble, and will, therefore, be removed with the quench water leaving the quench column. However, some of these contaminants are not very water soluble, and will not be removed in the quench column or in any non pressurized water wash following the quench column.

Oxygenates which can be considered as contaminants in a olefin stream include alcohols such as methanol, ethanol, $C_3$ alcohols; ethers such as dimethyl ether and methyl ethyl ether; carboxylic acids such as acetic acid, propanoic acid and butyric acid; aldehydes such as acetaldehyde; ketones such as acetone; and esters such as methyl esters. Particularly problematic oxygenate contaminants are dimethyl ether (DME) and acetaldehyde.

Dimethyl ether is particularly problematic, and is difficult to remove. It can be present in relatively high concentrations in the olefin produced from an oxygenate to olefin process, and is not very water soluble. This means that even after an olefin stream has gone through a quenching process, a substantial quantity of the dimethyl ether can remain in the olefin product.

Oxygenate contaminants can be removed to very low quantities in an olefin stream using an extractive distillation process under the appropriate conditions and with an appropriate extractant. Extractive distillation differs from the quench process in that olefin is distilled from the contaminant using an extractant to aid the distillation process.

Extractive distillation is carried out using a vessel or tower having internal packing or trays that creates a temperature difference from top to bottom of the tower. The upper portion of the tower is the cooler portion, and higher volatile components in the olefin exit from the top of the tower.

An extractant or solvent is added to the extractive distillation vessel or tower so as to enhance or suppress the volatility of the oxygenate relative to the olefin. This makes it easier to distill the oxygenate from the olefin, resulting in removal of the oxygenate to very low levels.

The extractive distillation process can be applied at any step in the purification and separation process. In one embodiment of the invention, the extractive distillation process occurs immediately after quenching of the product stream. In another embodiment, the product stream is quenched and then distilled into a $C_2^-$ hydrocarbon component and a $C_3^+$ hydrocarbon component. Most of the oxygenated hydrocarbons will be part of the $C_3^+$ hydrocarbon component. The extractive distillation process can then be applied to this component alone.

In another embodiment of the invention, an olefin stream containing oxygenate contaminant is contacted with quench water in a quench vessel. The quenched olefin product is recovered and sent to an extractive distillation vessel. The extractive distillation vessel is operated at an operating pressure which is higher than that of the quench vessel. In another embodiment, the operating temperature is also higher than that of the quench vessel.

Extractants which can be used in this invention are liquids at 1 atm. These exactants also desirably have an average boiling point of at least 100° F. (38° C.), preferably at least 120° F. (49° C.), and more preferably at least 150° F. (66° C.). Average boiling point, as defined herein, takes into account the boiling point of each compound in the extractant on a weight average basis. For example, an extractant containing 90 wt. % of a compound having a boiling point of 100 degrees and 10 wt. % of a compound having a boiling point of 200 degrees would have an average boiling point of 110 degrees.

The extractants are also desirably polar compositions. Such compositions preferably contain compounds such as water, monohydric alcohols, polyhydric alcohols, or mixtures thereof. Preferred monohydric alcohols include ethanol and propanol. Preferred polyhydric alcohols include glycols. Preferred glycols include ethylene glycol and tri-ethylene glycol. It is desirable that the extractant contain at least about 75 wt. % water, monohydric alcohol, and or polyhydric alcohol, preferably at least about 85 wt. %, more preferably at least about 90 wt. %, and most preferably at least about 95 wt. %. Water is most preferred as the extractant.

The extractive distillation vessel or column can be of conventional design. Preferably a packed distillation column is used.

The extractive distillation process is desirably operated at a pressure higher than the quench operating pressure. Preferably extractive distillation is carried out at an operating pressure of at least about 50 psi (345 kPa) higher than the quench, more preferably at least about 100 psi (689 kPa), and most preferably at least about 150 psi (1,034 kPa) higher. Preferably, the extractive distillation process is carried out at a pressure of from about 100 psia (689 kPa) to about 5000 psia (34,500 kPa). More preferred operating ranges are from about 150 psia (1,034 kPa) to about 4000 psia (27,000 kPa); about 200 psia (1,300 kPa) to about 3000 psia (21,000 kPa); about 250 psia (1,700 kPa) to about 2500 psia (17,000 kPa); and about 300 psia (2,100 kPa) to about 2000 psia (14,000 kPa). As the pressure in the extractive distillation vessel increases, the more oxygenate, particularly dimethyl ether, is removed from the olefin stream.

The extractive distillation process is particularly effective for removing very low concentrations of oxygenate present in an olefin stream. It is a very efficient process for removing oxygenate contaminant from an olefin stream which contains not greater than 20 wt. % oxygenates. Extractive distillation carried out according to this invention is even effective with olefin streams containing not greater than 10 wt. %, 5 wt. %, 1 wt. %, 0.5 wt. % or 0.1 wt. % oxygenate; particularly when the oxygenate is dimethyl ether.

In one embodiment of the invention, extractant is added to the top of an extractive distillation column, and is removed as a bottoms product from the bottom of the extractive distillation column. The extractive distillation column is desirably operated below the boiling point of the extractant, and above the boiling point of the product effluent at the operating pressure of the distillation column. As the extractant travels down the distillation column, oxygenated contaminants, including DME, are absorbed into the extractant, and removed along with the extractant as a liquid bottoms product from the extractive distillation column.

The extractive distillation process of this invention allows for the recovery of an olefin product having very low oxygenate contaminant levels. The total oxygenate content of the product stream, particularly an olefin stream containing at least 50 wt. % ethylene and propylene, can be about 10 wt. % or less, depending on the exact operating conditions of the extractive distillation process and the quantity of the oxygenates in the olefin stream to be purified. Olefin products having not greater than 5000 wt. ppm, 3000 wt. ppm, 2000 wt. ppm, 1000 wt. ppm, 500 wt. ppm, 250 wt. ppm, 100 wt. ppm, 50 wt. ppm, 10 wt. ppm and 5 wt. ppm oxygenates, particularly DME, are also readily achievable.

The DME-containing extractant leaving the extractive distillation column can be recovered and used after a regeneration process. Regeneration of the extractant can be accomplished by conventional means. Preferably, the extractant is regenerated by separating the extractant from absorbed compounds in a distillation column. Preferably, an extractant that has a boiling point temperature at least about 5° F., more preferably at least about 10° F. higher, than the absorbed compounds is used in the extractive distillation column.

The bottoms product from the extractive distillation column is fed into the distillation column for regeneration. The distillation column produces an overhead stream comprising oxygenates and hydrocarbons that were absorbed by the extractant in the extractive distillation column. The bottoms product from the distillation column is regenerated extractant that can be returned to the extractive distillation column. If water is used as the extractant, the DME-containing extractant can be combined with the water leaving the quench tower or other various water wash processes for regeneration. The oxygenate containing water can be distilled together in one or more distillation columns to remove the oxygenates.

Preferably, the extractant is cooled before being returned to the top of the extractive distillation column. Cooling the extractant below the temperature of the extractive distillation column's overhead product stream aids the efficiency of the column. In an extractive distillation column using water as the extractant, preferably the temperature of the extractant is cooled to below about 95° F. (35° C.), and more preferably the extractant is cooled to below about 90° F. (32° C.), before being returned to the extractive distillation column. The extractant can be cooled by conventional means.

In another embodiment, water or other extractant that can be used as an oxygenate feed or diluent in an oxygenate to olefin process is used as an extractant in the extractive distillation column. If a suitable extractant is used, the bottoms product from the extractive distillation column can be used as a co-feed to an oxygenate to olefin reactor without the use of a regeneration column.

The olefin containing stream, which is purified according to the process of this invention can be procured from an oxygenate to olefins process. In the oxygenate to olefin process, a feed containing an oxygenate, and optionally a diluent or a hydrocarbon added separately or mixed with the oxygenate, is contacted with an olefin forming catalyst to produce olefins and other hydrocarbons.

A preferred type of olefin forming catalyst is one containing a silicoaluminophosphate (SAPO) molecular sieve. Silicoaluminophosphate molecular sieves are generally classified as being microporous materials having 8, 10, or 12 membered ring structures. These ring structures can have an average pore size ranging from about 3.5–15 angstroms. Preferred are the small pore SAPO molecular sieves having an average pore size of less than about 5 angstroms, preferably an average pore size ranging from about 3.5 to 5 angstroms, more preferably from 3.5 to 4.2 angstroms. These pore sizes are typical of molecular sieves having 8 membered rings.

Substituted SAPOs can also be used in oxygenate to olefin reaction processes. These compounds are generally known as MeAPSOs or metal-containing silicoaluminophosphates. The metal can be alkali metal ions (Group IA), alkaline earth metal ions (Group IIA), rare earth ions (Group IIIB, including the lanthanoid elements: lanthanum, cerium, praseodymium, neodymium, samarium, europium, gadolinium, terbium, dysprosium, holmium, erbium, thulium, ytterbium and lutetium; and scandium or yttrium) and the additional transition cations of Groups IVB, VB, VIB, VIIB, VIIIB, and IB.

Preferably, the Me represents atoms such as Zn, Mg, Mn, Co, Ni, Ga, Fe, Ti, Zr, Ge, Sn, and Cr. These atoms can be inserted into the tetrahedral framework through a $[MeO_2]$ tetrahedral unit. The $[MeO_2]$ tetrahedral unit carries a net electric charge depending on the valence state of the metal substituent. When the metal component has a valence state of +2, +3, +4, +5, or +6, the net electric charge is between −2 and +2. Incorporation of the metal component is typically accomplished adding the metal component during synthesis of the molecular sieve. However, post-synthesis ion exchange can also be used. In post synthesis exchange, the metal component will introduce cations into ion-exchange positions at an open surface of the molecular sieve, not into the framework itself.

Suitable silicoaluminophosphate molecular sieves include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof. Preferred are SAPO-18, SAPO-34, SAPO-35, SAPO-44, and SAPO-47, particularly SAPO-18 and SAPO-34, including the metal containing forms thereof, and mixtures thereof. As used herein, the term mixture is synonymous with combination and is considered a composition of matter having two or more components in varying proportions, regardless of their physical state.

An aluminophosphate (ALPO) molecular sieve can also be included in the catalyst composition. Aluminophosphate molecular sieves are crystalline microporous oxides which can have an $AlPO_4$ framework. They can have additional elements within the framework, typically have uniform pore dimensions ranging from about 3 angstroms to about 10 angstroms, and are capable of making size selective separations of molecular species. More than two dozen structure types have been reported, including zeolite topological analogues. A more detailed description of the background and synthesis of aluminophosphates is found in U.S. Pat. No. 4,310,440, which is incorporated herein by reference in its entirety. Preferred ALPO structures are ALPO-5, ALPO-11, ALPO-18, ALPO-31, ALPO-34, ALPO-36, ALPO-37, and ALPO-46.

The ALPOs can also include a metal substituent in its framework. Preferably, the metal is selected from the group consisting of magnesium, manganese, zinc, cobalt, and mixtures thereof. These materials preferably exhibit adsorption, ion-exchange and/or catalytic properties similar to aluminosilicate, aluminophosphate and silica aluminophosphate molecular sieve compositions. Members of this class and their preparation are described in U.S. Pat. No. 4,567,029, incorporated herein by reference in its entirety.

The metal containing ALPOs have a three-dimensional microporous crystal framework structure of $MO_2$, $Al_2$ and $PO_2$ tetrahedral units. These as manufactured structures (which contain template prior to calcination) can be represented by empirical chemical composition, on an anhydrous basis, as:

mR: $(M_xAl_yP_z)O_2$ wherein "R" represents at least one organic templating agent present in the intracrystalline pore system; "m" represents the moles of "R" present per mole of $(M_xAl_yP_z)O_2$ and has a value of from zero to 0.3, the maximum value in each case depending upon the molecular dimensions of the templating agent and the available void volume of the pore system of the particular metal aluminophosphate involved, "x", "y", and "z" represent the mole fractions of the metal "M", (i.e. magnesium, manganese, zinc and cobalt), aluminum and phosphorus, respectively, present as tetrahedral oxides.

The metal containing ALPOs are sometimes referred to by the acronym as MeAPO. Also in those cases where the metal "Me" in the composition is magnesium, the acronym MAPO is applied to the composition. Similarly ZAPO, MNAPO and CoAPO are applied to the compositions which contain zinc, manganese and cobalt respectively. To identify the various structural species which make up each of the sub-generic classes MAPO, ZAPO, CoAPO and MNAPO, each species is assigned a number and is identified, for example, as ZAPO-5, MAPO-11, CoAPO-34 and so forth.

The silicoaluminophosphate molecular sieve is typically admixed (i.e., blended) with other materials. When blended, the resulting composition is typically referred to as a SAPO catalyst, with the catalyst comprising the SAPO molecular sieve.

Materials which can be blended with the molecular sieve can be various inert or catalytically active materials, or various binder materials. These materials include compositions such as kaolin and other clays, various forms of rare earth metals, metal oxides, other non-zeolite catalyst components, zeolite catalyst components, alumina or alumina sol, titania, zirconia, magnesia, thoria, beryllia, quartz, silica or silica or silica sol, and mixtures thereof. These components are also effective in reducing, inter alia, overall catalyst cost, acting as a thermal sink to assist in heat shielding the catalyst during regeneration, densifying the catalyst and increasing catalyst strength. It is particularly desirable that the inert materials that are used in the catalyst to act as a thermal sink have a heat capacity of from about 0.05 to about 1 cal/g-° C., more preferably from about 0.1 to about 0.8 cal/g-° C., most preferably from about 0.1 to about 0.5 cal/g-° C.

Additional molecular sieve materials can be included as a part of the SAPO catalyst composition or they can be used as separate molecular sieve catalysts in admixture with the SAPO catalyst if desired. Structural types of small pore molecular sieves that are suitable for use in this invention include AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof. Structural types of medium pore molecular sieves that are suitable for use in this invention include MFI, MEL, MTW, EUO, MTT, HEU, FER, AFO, AEL, TON, and substituted forms thereof. These small and medium pore molecular sieves are described in greater detail in the *Atlas of zeolite Structural Types*, W. M. Meier and D. H. Olsen, Butterworth Heineman, 3rd ed., 1997, the detailed description of which is explicitly incorporated herein by reference. Preferred molecular sieves which can be combined with a silicoaluminophosphate catalyst include ZSM-5, ZSM-34, erionite, and chabazite.

The catalyst composition preferably comprises about 1% to about 99%, more preferably about 5% to about 90%, and most preferably about 10% to about 80%, by weight of molecular sieve. It is also preferred that the catalyst composition have a particle size of from about 20 T to 3,000 T, more preferably about 30 T to 200 T, most preferably about 50 T to 150 T.

The catalyst can be subjected to a variety of treatments to achieve the desired physical and chemical characteristics. Such treatments include, but are not necessarily limited to hydrothermal treatment, calcination, acid treatment, base treatment, milling, ball milling, grinding, spray drying, and combinations thereof.

The oxygenate feed is contacted with the chosen catalyst in a reaction zone or volume. The volume in which such contact takes place is herein termed the "reactor," which may be a part of a "reactor apparatus" or "reaction system." Another part of the reaction system may be a "regenerator," which comprises a volume wherein carbonaceous deposits (or coke) on the catalyst resulting from the olefin conversion reaction are removed by contacting the catalyst with regeneration medium.

The oxygenate feed that can be used in the oxygenate to olefin process comprises at least one organic compound which contains at least one oxygen atom, such as aliphatic alcohols, ethers, carbonyl compounds (aldehydes, ketones, carboxylic acids, carbonates, esters and the like). When the oxygenate is an alcohol, the alcohol can include an aliphatic moiety having from 1 to 10 carbon atoms, more preferably from 1 to 4 carbon atoms. Representative alcohols include but are not necessarily limited to lower straight and branched chain aliphatic alcohols and their unsaturated counterparts. Examples of suitable oxygenate compounds include, but are not limited to: methanol; ethanol; n-propanol; isopropanol; $C_4$–$C_{20}$ alcohols; methyl ethyl ether; dimethyl ether; diethyl ether; di-isopropyl ether; formaldehyde; dimethyl carbonate; dimethyl ketone; acetic acid; and mixtures thereof. Preferred oxygenate compounds are methanol, dimethyl ether, or a mixture thereof.

One or more inert diluents may be present in the feedstock, for example, in an amount of from 1 to 99 molar percent, based on the total number of moles of all feed and diluent components fed to the reaction zone (or catalyst). As defined herein, diluents are compositions which are essentially non-reactive across a molecular sieve catalyst, and primarily function to make the oxygenates in the feedstock less concentrated. Typical diluents include, but are not necessarily limited to helium, argon, nitrogen, carbon monoxide, carbon dioxide, water, essentially non-reactive paraffins (especially the alkanes such as methane, ethane, and propane), essentially non-reactive alkylenes, essentially non-reactive aromatic compounds, and mixtures thereof. The preferred diluents are water and nitrogen. Water can be injected in either liquid or vapor form.

Hydrocarbons can also be included as part of the feedstock, i.e., as co-feed. As defined herein, hydrocarbons included with the feedstock are hydrocarbon compositions which are converted to another chemical arrangement when contacted with molecular sieve catalyst. These hydrocarbons can include olefins, reactive paraffins, reactive alkylaromatics, reactive aromatics or mixtures thereof. Preferred hydrocarbon co-feeds include, propylene, butylene, pentylene, $C_4^+$ hydrocarbon mixtures, $C_5^+$ hydrocarbon mixtures, and mixtures thereof. More preferred as co-feeds are a $C_4^+$ hydrocarbon mixtures, with the most preferred being $C_4^+$ hydrocarbon mixtures which are obtained from separation and recycle of reactor product.

Any standard reactor system can be used in the oxygenate to olefin process, including fixed bed, fluid bed or moving bed systems. Preferred reactors are co-current riser reactors and short contact time, countercurrent free-fall reactors. Desirably, the reactor is one in which an oxygenate feedstock can be contacted with a molecular sieve catalyst at a weight hourly space velocity (WHSV) of at least about 1 $hr^{-1}$, preferably from about 1 $hr^{-1}$ to about 1000 $hr^{-1}$, more preferably from about 20 $hr^{-1}$ to about 1000 $hr^{-1}$, and most preferably from about 20 $hr^{-1}$ to about 500 $hr^{-1}$. WHSV is defined herein as the weight of oxygenate, and hydrocarbon which may optionally be in the feed, per hour per weight of the molecular sieve content of the catalyst. Because the catalyst or the feedstock may contain other materials which act as inerts or diluents, the WHSV is calculated on the weight basis of the oxygenate feed, and any hydrocarbon which may be present, and the molecular sieve contained in the catalyst.

Preferably, the oxygenate feed is contacted with the catalyst when the oxygenate is in a vapor phase. Alternately, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions.

The process can generally be carried out at a wide range of temperatures. An effective operating temperature can be from about 200° C. to about 700° C., preferably from about 300° C. to about 600° C., more preferably from about 350° C. to about 550° C. At the lower end of the temperature range, the formation of the desired olefin products may become markedly slow. At the upper end of the temperature range, the process may not form an optimum amount of product.

The pressure in the oxygenate to olefin process also may vary over a wide range, including autogenous pressures. Effective pressures may be in, but are not necessarily limited to, oxygenate partial pressures at least about 1 psia (7 kPa), preferably at least about 5 psia (35 kPa). The process is particularly effective at higher oxygenate partial pressures, such as an oxygenate partial pressure of greater than about 20 psia (130 kPa). Preferably, the oxygenate partial pressure is at least about 25 psia (170 kPa), more preferably at least about 30 psia (210 kPa). For practical design purposes it is desirable to operate at a methanol partial pressure of not greater than about 500 psia (3,450 kPa), preferably not greater than about 400 psia (2,700 kPa), most preferably not greater than about 300 psia (2,100 kPa).

One skilled in the art will also appreciate that the olefins purified according to the present invention can be polymerized to form polyolefins, particularly polyethylene and polypropylene. In one embodiment, the olefin containing stream is purified according to the invention, and at least one of the olefins in the purified stream is polymerized. It is desirable that following the purification process, the purified olefin is further separated into olefin components and at least one of the olefin components is purified. The invention is particularly desirable for polymerizing polypropylene.

Processes for forming polyolefins from olefins are known in the art. Catalytic processes are preferred. Particularly preferred are metallocene, Zieglar/Natta and acid catalytic systems. See, for example, U.S. Pat. Nos. 3,258,455; 3,305, 538; 3,364,190; 5,892,079; 4,659,685; 4,076,698; 3,645, 992; 4,302,565; and 4,243,691, the catalyst and process descriptions of each being expressly incorporated herein by reference. In general, these methods involve contacting the olefin product with a polyolefin-forming catalyst at a pressure and temperature effective to form the polyolefin product.

A preferred polyolefin-forming catalyst is a metallocene catalyst. The preferred temperature range of operation is between about 50° C. and about 240° C. and the reaction can be carried out at low, medium or high pressure, being anywhere from about 1 to about 200 bars. For processes carried out in solution, an inert diluent can be used, and the preferred operating pressure is from about 10 to about 150 bars, with a preferred temperature of from about 120° C. to about 230° C. For gas phase processes, it is preferred that the temperature generally be from about 60° C. to about 160° C., and that the operating pressure be from about 5 to about 50 bars.

In addition to polyolefins, numerous other olefin derivatives may be formed from the olefins recovered therefrom. These include, but are not limited to, aldehydes, alcohols, acetic acid, linear alpha olefins, vinyl acetate, ethylene dicholoride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes. The methods of manufacturing these derivatives are well known in the art, and therefore, are not discussed herein.

A flow diagram of one embodiment of the invention, which combines the water quench and extractive distillation processes, is shown in the FIGURE. A methanol containing feed stream 10 is fed into oxygenate to olefin reactor 12. The oxygenate to olefin reactor 12 contains a SAPO-34 catalyst that converts the methanol feed stream 12 into an effluent 14 containing a variety of non-oxygenated hydrocarbons and oxygenated compounds. The gaseous effluent stream 14 is fed into a bottom portion of a quench column 18. Water 16 is fed into a top portion of the quench column 18 at a temperature and rate sufficient to condense a significant quantity of water and unreacted feed which can be present in effluent stream 14. Quench column 18 preferably contains packing that aids heat transfer and mixing of the gaseous effluent stream 14 and the cooling water 16. Stream 20, the bottoms from the quench column 18, contains warmed quenching water 16, condensed water, absorbed oxygenates and condensed unreacted methanol from effluent stream 14. Stream 22 the overhead stream from the quench column 18 contains olefin and hydrocarbon products along with oxygenates that were not completely absorbed by the water in the quench column, these oxygenates include dimethyl ether and acetaldehyde. Stream 22 is fed into a series of compressor 24. Compressor series 24 preferably compresses stream 22 to a pressure of preferably around 300 psia forming compressed stream 26.

Compressed stream 26 is fed into extractive distillation column 30. Extractant water stream 28 is fed into a top portion of extractive distillation column 30 at about 6 times by weight of the compressed stream 26. Extractive distillation column 28 contains a packing that allows for good contact between gasses and liquids within the column. The extractant water 28 is fed into the distillation column at about 90° F. The extractive distillation column preferably operates at about 300 psia and produces an overhead stream 32 which contains olefin and hydrocarbon products with dimethyl ether and acetaldehyde removed. The overhead stream exits the extractive distillation column 30 at a temperature of about 90° F. and goes to further processing which can include separation process for separating the overhead stream into separate product streams and the further removal of various contaminants.

Bottoms stream 34 from extractive distillation column 30 comprises water extractant along with absorbed oxygenates including dimethyl ether and acetaldehyde and some absorbed olefins and hydrocarbon components. Bottoms stream 34 is fed into oxygenate stripping column 36. Oxygenate stripping column 36 splits the water and oxygenate containing stream 34 into a bottoms product 40 comprising water and a overhead stream 38 comprising oxygenates and hydrocarbons. Water stream 40 is cooled by heat exchanger 42 to produce extractant stream 28 which is fed into the extractive distillation column 36. Oxygenate and hydrocarbon stream 38 is sent back to the oxygenate to olefin reactor 12 to produce more olefin and hydrocarbon products.

This invention is further described in the following examples, which represent various embodiments of the overall invention.

EXAMPLE 1

A gas effluent stream from an oxygenate to olefins (OTO) reactor containing a SAPO-34 catalyst is partially condensed at a temperature of 100° F. and a pressure of 40 psia in a settling tank. The vapor from the settling tank is removed from the settling tank at a flow rate of 1.20 lb-mol/hr. The vapor from the settling tank contains various hydrocarbon products including ethylene and propylene along with various contaminants. The contaminants include 1.28 wt % water and 1.85 wt % oxygenated hydrocarbons. The oxygenated hydrocarbon DME is present in the vapor stream at 0.995 wt %. The oxygenated hydrocarbon acetaldehyde is present in the vapor stream at 0.32 wt %.

The vapor stream from the settling tank was fed to a wash column at 40 psia and 100° F. The wash column has 10 trays. The vapor feed stream is fed into the column below the 10 tray. A liquid water stream is fed into the wash column above the first tray at a rate of 8.881 lb-mol/hr, a temperature of 40° F. and a pressure of 40 psia. A vapor phase product stream is removed from the wash column as an overhead product. The overhead from the wash column contains the hydrocarbon products and is removed at a rate of 1.183 lb-mol/hr, a temperature of 90.3° F. and a pressure of 40 psia. The overhead from the wash column contains 0.95 wt % water and 0.81 wt % oxygenated hydrocarbons. The oxygenated hydrocarbon DME is present in the vapor stream at 0.71 wt %. The oxygenated hydrocarbon acetaldehyde is present in the vapor stream at 0.10 wt %.

The vapor overhead stream from the wash column is compressed and fed into a pressurized extractive distillation column operating at 300 psia and 275.6° F. The extractive distillation column has 39 trays plus a reboiler. The vapor stream from the wash column is fed into the extractive distillation column below the 39 plate. Water is used as an extractant and is fed into the column above the first plate at a flow rate of 6.66 lb-mol/hr and a temperature of 90° F. The vapor overhead stream from the extractive distillation column contains the hydrocarbon products and is removed at a flow rate of 1.15 lb-mol/hr, a temperature of 90.2° F. and a pressure of 300 psia. The overhead stream from the extractive distillation column contains 0.14 wt % water and less than 1 ppm oxygenated hydrocarbons including DME and acetaldehyde.

EXAMPLE 2

The same process is followed as in Example 1, except that the overhead stream from the wash column is compressed to a pressure of 250 psia and a temperature of 257.4° F. Water is again used as the extractant in the extractive distillation column and is fed into the column above the first plate at a flow rate of 6.66 lb-mol/hr and a temperature of 90° F. The vapor overhead stream from the extractive distillation column contains the hydrocarbon products and is removed at a flow rate of 1.16 lb-mol/hr, a temperature of 90.1° F. and a pressure of 250 psia. The overhead stream from the extractive distillation column contains 0.17 wt % water, 1 ppm DME and less than 1 ppm other oxygenated hydrocarbons including acetaldehyde.

EXAMPLE 3

The same process is followed as in Example 1, except that the overhead stream from the wash column is compressed to a pressure of 200 psia and a temperature of 235.7° F. Water is again used as the extractant in the extractive distillation column and is fed into the column above the first plate at a flow rate of 6.66 lb-mol/hr and a temperature of 90° F. The vapor overhead stream from the extractive distillation column contains the hydrocarbon products and is removed at a flow rate of 1.16 lb-mol/hr, a temperature of 90.2° F. and a pressure of 200 psia. The overhead stream from the extractive distillation column contains 0.20 wt % water, 325 ppm DME and less than 1 ppm other oxygenated hydrocarbons including acetaldehyde.

EXAMPLE 4

The same process is followed as in Example 1, except that the overhead stream from the wash column is compressed to a pressure of 150 psia and a temperature of 208.3° F. Water is again used as the extractant in the extractive distillation column and is fed into the column above the first plate at a flow rate of 6.661 lb-mol/hr and a temperature of 90° F. The vapor overhead stream from the extractive distillation column contains the hydrocarbon products and is removed at a flow rate of 1.16 lb-mol/hr, a temperature of 90.2° F. and a pressure of 200 psia. The overhead stream from the extractive distillation column contains 0.27 wt % water, 2,286 ppm DME and less than 1 ppm other oxygenated hydrocarbons including acetaldehyde.

Example 1 shows that if the extractive distillation column is operated at a pressure of 300 psia essentially all measurable amounts of oxygenated hydrocarbons, including DME, can be removed. As the pressure is decreased, the effectiveness of the extractive distillation column in removing DME decreases as shown in Examples 2–4. However, Example 4 further shows that the extractive distillation column is still effective in removing essentially all measurable amounts of oxygenates, except for DME, at lower pressures.

Having now fully described this invention, it will be appreciated by those skilled in the art that the invention can be performed within a wide range of parameters within what is claimed, without departing from the spirit and scope of the invention.

What is claimed is:

1. A method of extracting an oxygenate from an olefin containing stream, comprising:

contacting the olefin containing stream with an extractant; and separating the contacted olefin containing stream and extractant using extractive distillation, wherein the olefin containing stream comprises at least 50 wt. % olefins and not greater than 20 wt. % oxygenates prior to contact with the extractant, and the extractant is a polar liquid composition at 1 atm., having an average boiling point of at least 100° F. (38° C.) at 1 atm.

2. The method of claim 1, wherein the polar liquid composition comprises at least 75 wt. % water, alcohol, or a mixture thereof.

3. The method of claim 1, wherein the polar liquid composition comprises at least 75 wt. % water.

4. The method of claim 1, wherein the polar liquid composition comprises at least 75 wt. % alcohol.

5. The method of claim 2 or 4, wherein the alcohol is ethanol, propanol, a glycol, or a mixture thereof.

6. The method of claim 1, wherein the oxygenates comprise dimethyl ether.

7. The method of claim 1, wherein the oxygenates comprise acetaldehyde.

8. The method of claim 1, wherein the extractive distillation is carried out at a pressure of from 100 psia to 5000 psia.

9. The method of claim 8, wherein the extractive distillation is carried out at a pressure of from 150 psia to 4000 psia.

10. The method of claim 9, wherein the extractive distillation is carried out at a pressure of from 200 psia to 3000 psia.

11. The method of claim 10, wherein the extractive distillation is carried out at a pressure of from 250 psia to 2500 psia.

12. The method of claim 11, wherein the extractive distillation is carried out at a pressure of from 300 psia to 2000 psia.

13. The method of claim 1, wherein the olefin containing stream, prior to contact with the extractant, contains at least 50 wt. % ethylene and propylene.

14. A method of purifying an olefin containing stream, comprising:

contacting the olefin containing stream with a water containing stream in a first vessel;

recovering olefin product from the first vessel; and contacting the olefin product from the first vessel with an extractant in a second vessel at a temperature and pressure higher than that of the first vessel, wherein the olefin containing stream, prior to contact with the extractant, comprises an oxygenate and at least 50 wt. % ethylene and propylene, and the extractant is a polar liquid composition at 1 atm., having an average boiling point of at least 100° F. (38° C.) at 1 atm.

15. The method of claim 14, wherein the polar liquid composition comprises at least 75 wt. % water, alcohol, or a mixture thereof.

16. The method of claim 14, wherein the polar liquid composition comprises at least 75 wt. % water.

17. The method of claim 14, wherein the polar liquid composition comprises at least 75 wt. % alcohol.

18. The method of claim 15 or 17, wherein the alcohol is ethanol, propanol, a glycol, or a mixture thereof.

19. The method of claim 14, wherein the oxygenates comprise dimethyl ether.

20. The method of claim 14, wherein the oxygenates comprise acetaldehyde.

21. The method of claim 14, wherein the contacting is carried out at a pressure of from 100 psia to 5000 psia.

22. The method of claim 15, wherein the contacting is carried out at a pressure of from 150 psia to 4000 psia.

23. The method of claim 16, wherein the contacting is carried out at a pressure of from 200 psia to 3000 psia.

24. The method of claim 17, wherein the contacting is carried out at a pressure of from 250 psia to 2500 psia.

25. The method of claim 18, wherein the contacting is carried out at a pressure of from 300 psia to 2000 psia.

26. A method of purifying and polymerizing an olefin containing stream, comprising:

contacting the olefin containing stream with a water containing stream in a first vessel;

recovering olefin product from the first vessel;

contacting the olefin product from the first vessel with an extractant in a second vessel at a temperature and pressure higher than that of the first vessel, wherein the olefin containing stream, prior to contact with the extractant, comprises at least 50 wt. % ethylene and propylene, and the extractant is a polar liquid composition at 1 atm., having an average boiling point of at least 100° F. (38° C.) at 1 atm;

recovering olefin product from the second vessel; and polymerizing at least one olefin recovered from the second vessel.

* * * * *